(12) United States Patent
Lin et al.

(10) Patent No.: US 9,261,527 B2
(45) Date of Patent: Feb. 16, 2016

(54) METHOD OF UTILIZING MOBILE DEVICE TO DETECT EMERGENCY AND RELATED EMERGENCY DETECTING SYSTEM

(71) Applicant: Wistron Corporation, New Taipei (TW)

(72) Inventors: Wei-Chih Lin, New Taipei (TW);
Chih-Ping Huang, New Taipei (TW);
Yuan-Chan Lee, New Taipei (TW)

(73) Assignee: Wistron Corporation, Hsichih, New Taipei (TW)

( * ) Notice: Subject to any disclaimer, the term of this patent is extended or adjusted under 35 U.S.C. 154(b) by 78 days.

(21) Appl. No.: 14/085,812

(22) Filed: Nov. 21, 2013

(65) Prior Publication Data
US 2014/0338445 A1   Nov. 20, 2014

(30) Foreign Application Priority Data

May 14, 2013   (TW) .............................. 102117052 A

(51) Int. Cl.
*G08B 21/02* (2006.01)
*G01P 15/08* (2006.01)
*A61B 5/11* (2006.01)

(52) U.S. Cl.
CPC ........... *G01P 15/0891* (2013.01); *A61B 5/1117* (2013.01)

(58) Field of Classification Search
CPC .................... A61B 5/1117; A61B 2562/0219; G08B 21/0446; G08B 23/00; G08B 21/02; G08B 23/02; G01V 7/00; G01P 15/0891; G01P 15/00; G01M 7/00
USPC ................ 340/573.1, 539.11; 73/865.4, 1.01, 73/382 R, 488; 455/404.1, 404.2; 600/300, 600/301

See application file for complete search history.

(56) References Cited

U.S. PATENT DOCUMENTS

| | | | |
|---|---|---|---|
| 7,248,172 B2 * | 7/2007 | Clifford et al. ............ | 340/573.1 |
| 8,381,603 B2 * | 2/2013 | Peng et al. .................. | 73/865.4 |
| 2007/0037619 A1 * | 2/2007 | Matsunaga et al. ........ | 455/575.7 |
| 2010/0323657 A1 | 12/2010 | Barnard | |
| 2011/0316702 A1 | 12/2011 | Chuang | |
| 2012/0182189 A1 | 7/2012 | Wu | |
| 2013/0135097 A1 * | 5/2013 | Doezema ................. | 340/539.13 |
| 2013/0178174 A1 * | 7/2013 | Geris et al. .................. | 455/90.3 |

FOREIGN PATENT DOCUMENTS

| | | |
|---|---|---|
| TW | 201201148 | 1/2012 |
| TW | 201240402 | 10/2012 |

OTHER PUBLICATIONS

Office action mailed on Nov. 11, 2014 for the Taiwan application No. 102117052, filing date: May 14, 2013, p. 1 line 10-14, p. 2 and p. 3 line 1-19 and line 23-25.

* cited by examiner

*Primary Examiner* — Hung T Nguyen
(74) *Attorney, Agent, or Firm* — Winston Hsu; Scott Margo

(57) ABSTRACT

A method of utilizing a mobile device to detect an emergency includes detecting whether the mobile device is carried by a user; detecting an acceleration status of the mobile device when the mobile device is determined to be carried by the user; and determining whether the user is in the emergency according to the acceleration status of the mobile device.

17 Claims, 4 Drawing Sheets

METHOD OF UTILIZING MOBILE DEVICE TO DETECT EMERGENCY AND RELATED EMERGENCY DETECTING SYSTEM

BACKGROUND OF THE DISCLOSURE

1. Field of the Disclosure

The present disclosure relates to a method of utilizing a mobile device to detect an emergency, and more particularly, to a method of detecting an emergency and determining whether a user is involved in the emergency according to an acceleration status of a mobile device carried by the user.

2. Description of the Prior Art

As the average wealth of a nation increases, people start to place more importance on their quality of life and the security of their family. Security monitoring devices which integrate various fields such as burglar alarms, entrance management and remote monitoring can be utilized for personal safety and protection of property. As the related technology matures, various digitized, networking or integrated security products and applications have become commercially available. Most modern security monitoring products and applications are realized by monitors or security systems. Coverage of such monitors and security systems, however, may not be satisfactory. If an accident or emergency occurs in a place not covered by the monitors or security systems, the circumstances will not be known, and follow-up assistance or appropriate handling cannot be performed. Thus, how to immediately detect and determine whether a user is involved in an emergency has become a main focus of the industry. Such functionality can enable assistance or processing to be performed immediately after an emergency, in order to achieve effective monitoring for personal safety.

SUMMARY OF THE DISCLOSURE

It is therefore an objective of the present disclosure to provide a method of detecting an emergency, which is capable of determining whether a user is involved in an emergency according to an acceleration status of a mobile device, in order to enable immediate assistance or processing to be performed.

The present disclosure discloses a method of utilizing a mobile device to detect an emergency. The method comprises detecting whether the mobile device is carried by a user; detecting an acceleration status of the mobile device when the mobile device is determined to be carried by the user; and determining whether the user is in the emergency according to the acceleration status of the mobile device.

The present disclosure further discloses an emergency detecting system used in a mobile device. The emergency detecting system comprises a biosensor, for detecting whether the mobile device is carried by a user; a gravity sensor (G-sensor), for detecting an acceleration status of the mobile device; and a control module, coupled to the biosensor and the gravity sensor. The control module comprises a storage device, for storing a program; and a processor, for executing the program stored in the storage device, in order to perform the following steps: determining whether the mobile device is carried by the user; and determining whether the user is in an emergency according to the acceleration status of the mobile device when the mobile device is determined to be carried by the user.

The present disclosure further discloses a non-transitory computer-readable storage medium, having a program executable by a processor to perform the method of detecting an emergency mentioned above.

These and other objectives of the present disclosure will no doubt become obvious to those of ordinary skill in the art after reading the following detailed description of the preferred embodiment that is illustrated in the various figures and drawings.

DETAILED DESCRIPTION

Figure 1:
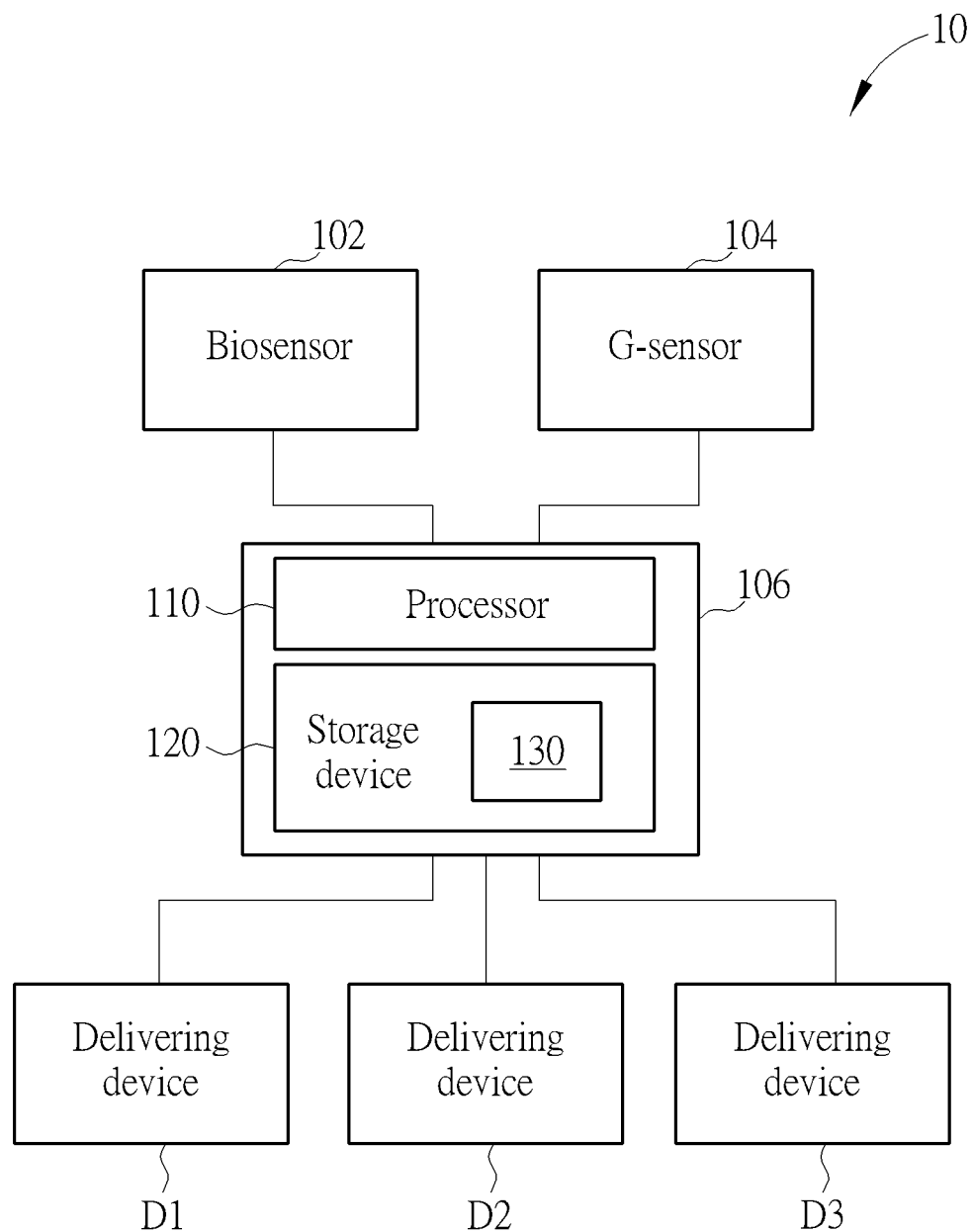
FIG. 1 is a schematic diagram of an emergency detecting system according to an embodiment of the present disclosure.

Please refer to FIG. 1, which is a schematic diagram of a mobile device 10 according to an embodiment of the present disclosure. The mobile device 10 may be a mobile phone, smart phone, portable media player, tablet, etc. For the sake of simplicity, only the devices utilized for realizing an emergency detecting system in the mobile device 10 are illustrated in FIG. 1. These devices may include a biosensor 102, a gravity sensor (G-sensor) 104, a control module 106 and delivering devices D1-D3. Other components or modules such as a display screen, audio device, microphone or camera may be disposed arbitrarily according to system requirements, and are omitted in FIG. 1 since these components do not affect the illustration of the present embodiment. In detail, the biosensor 102 is utilized for using biosensing technology to detect whether the mobile device 10 is carried by a user. The biosensor 102 may be a specific absorption rate (SAR) detector. Many countries in the world define a standard for limiting the SAR value of mobile devices, wherein any mobile devices that may emit electromagnetic waves have to pass the SAR test. The SAR refers to the rate of electromagnetic waves absorbed by a unit mass of organism in a unit of time. When the organism is closer to the mobile device, there is greater possibility of it being harmed by the electromagnetic waves. In such a condition, the value detected by the SAR detector may also increase, and this value may be utilized for determining whether the mobile device is carried by a user. In general, unless the user wears a cloth made of special material which may isolate electromagnetic waves, the SAR detector may function normally.

Please keep referring to FIG. 1. The gravity sensor 104 is utilized for detecting the physical quantities of the mobile device 10 such as movement, speed and acceleration. The gravity sensor 104 is able to accurately detect any variations of the mobile device 10, even tiny vibrations. Such variations or vibrations may generate corresponding coordinate information, which may be calculated using specific formulas that can be converted into a signal receivable by the mobile device 10, e.g. a voltage signal. When an emergency occurs, the acceleration may be affected. The control module 106 can therefore use the gravity sensor 104 to detect the acceleration status of the mobile device 10, in order to determine whether the user is in an emergency. The gravity sensor 104 should perform the detection together with the biosensor 102, in order to ensure that the user is carrying the mobile device 10. In detail, the biosensor 102 may keep detecting the relationship between the mobile device 10 and the user, wherein the mobile device 10 may be carried by the user, may be near the user or may be at a distance from the user. The control module 106 can only use the physical quantities provided by the gravity sensor 104 to determine whether the user is in an emergency when the mobile device 10 is carried by the user. If the mobile device 10 is not carried by the user the acceleration status may still undergo some variation (e.g. the mobile phone may fall off a table due to external vibrations, or the mobile phone may be contained in a backpack carried by the user), but these variations will not indicate whether the user is in an emergency.

Please keep referring to FIG. 1. The control module 106 is coupled to the biosensor 102 and the gravity sensor 104, and receives information from both the biosensor 102 and the gravity sensor 104. The control module 106 includes a processor 110 and a storage device 120. The storage device 120 may be of any type, and is utilized for storing a program code 130 to be read and executed by the processor 110. For example, the storage device 120 may be, but should not be limited to, a read-only memory (ROM), random-access memory (RAM), CD-ROM, magnetic tape, floppy disk, optical data storage device, etc. The processor 110 may be a microprocessor or an application-specific integrated circuit (ASIC) for executing the program code 130 stored in the storage device 120, in order to determine whether the user is in an emergency according to the information received from the biosensor 102 and the gravity sensor 104. The delivering devices D1-D3 are utilized for delivering alarm signals to notify the user or other people when an emergency occurs, to enable follow-up assistance or handling. The delivering devices D1-D3 may include any type of device that can generate signals in any form. In addition, the number of delivering devices may be determined according to system requirements, and is not limited herein.

Figure 2:
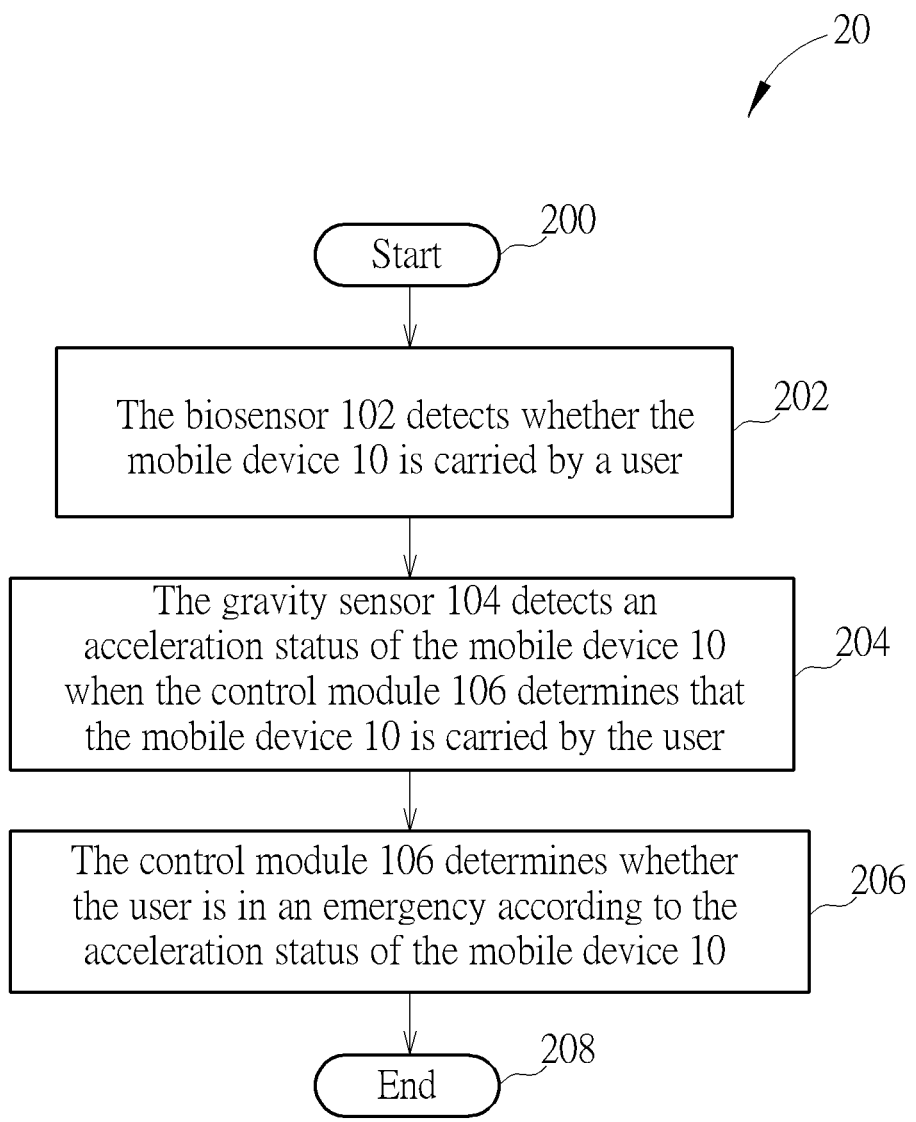
FIG. 2 is a schematic diagram of an emergency detecting process according to an embodiment of the present disclosure.

The above operations of the emergency detecting system in the mobile device 10 can be summarized into an emergency detecting process 20, as shown in FIG. 2. The emergency detecting process 20 may be compiled into the program code 130 to be stored in the storage device 120 and includes the following steps:

Step 200: Start.
Step 202: The biosensor 102 detects whether the mobile device 10 is carried by a user.
Step 204: The gravity sensor 104 detects an acceleration status of the mobile device 10 when the control module 106 determines that the mobile device 10 is carried by the user.
Step 206: The control module 106 determines whether the user is in an emergency according to the acceleration status of the mobile device 10.
Step 208: End.

The abovementioned emergency may include any situations that may place the user in harm, such as falling over, bumping into an object or falling from a height. The control module 106 determines various types of possible emergencies based on the acceleration information detected by the gravity sensor 104. The variations in acceleration usually correspond to different types of emergencies. For example, if a user falls from a height, the acceleration detected by the gravity sensor 104 may be towards the direction of gravitational acceleration and comply with a status of free fall, and this acceleration may persist for a period of time. If a user falls over or bumps into an object, the gravity sensor 104 may detect an instant variation on the acceleration, where this variation is greater than a specific magnitude. The determination procedures and methods for different types of emergencies may be slightly different.

Figure 3:
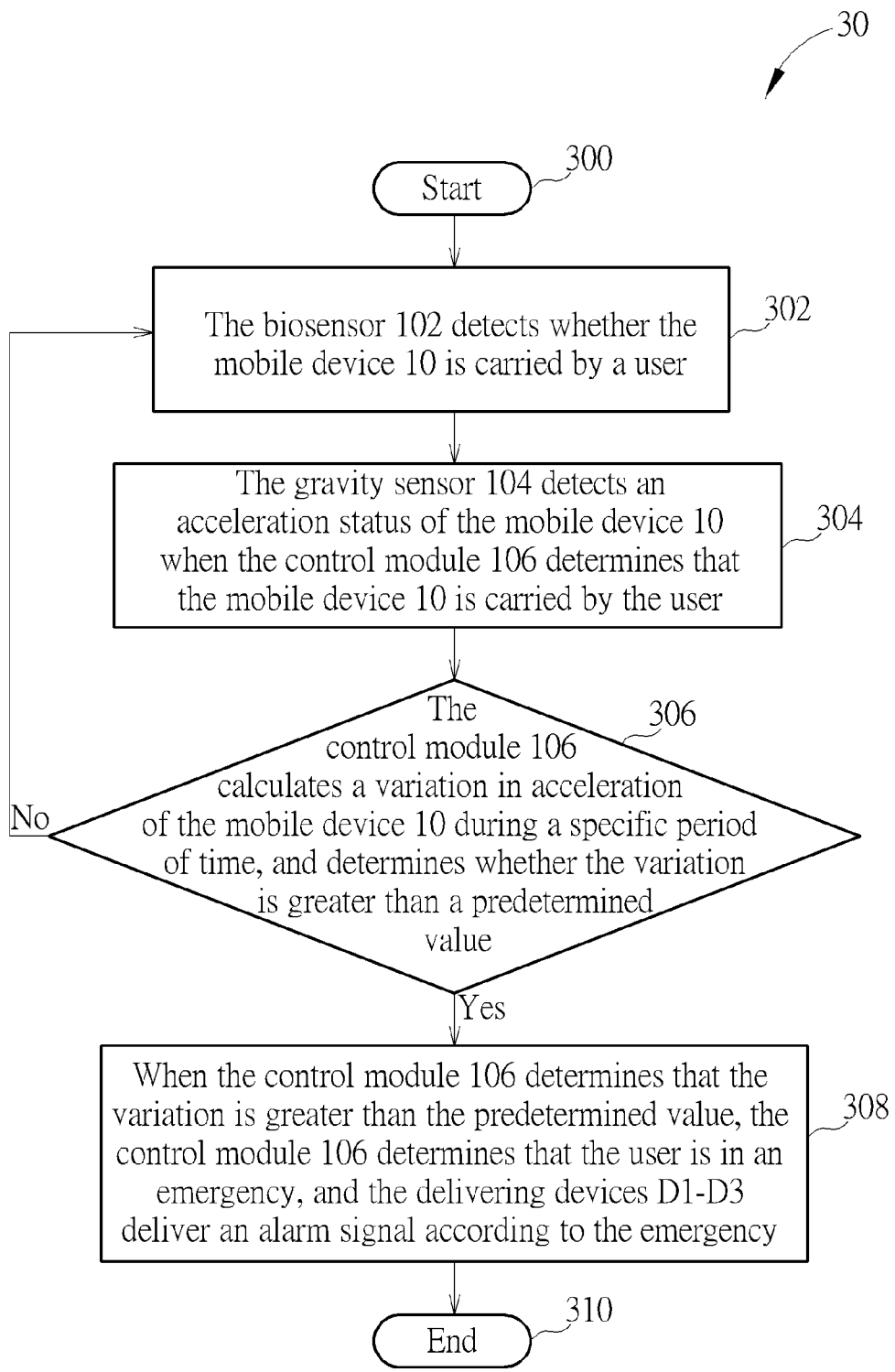
FIG. 3 is a schematic diagram of another emergency detecting process according to an embodiment of the present disclosure.

For an illustration of the above, please refer to FIG. 3, which is a schematic diagram of another emergency detecting process 30 according to an embodiment of the present disclosure. The emergency detecting process 30 may be utilized in the mobile device 10 and compiled into the program code 130 to be stored in the storage device 120. The emergency detecting process 30 may be realized in the above emergency detecting system, for the condition that the user falls over or the user bumps into an object. The emergency detecting process 30 includes the following steps:

Step 300: Start.
Step 302: The biosensor 102 detects whether the mobile device 10 is carried by a user.
Step 304: The gravity sensor 104 detects an acceleration status of the mobile device 10 when the control module 106 determines that the mobile device 10 is carried by the user.
Step 306: The control module 106 calculates a variation in acceleration of the mobile device 10 during a specific period of time, and determines whether the variation is greater than a predetermined value. If yes, the flow proceeds to Step 308; otherwise, the process returns to Step 302.
Step 308: When the control module 106 determines that the variation is greater than the predetermined value, the control module 106 determines that the user is in an emergency, and the delivering devices D1-D3 deliver an alarm signal according to the emergency.
Step 310: End.

According to the emergency detecting process 30, the biosensor 102 first detects whether the mobile device 10 is carried by the user. When the control module 106 determines that the mobile device 10 is carried by the user, the gravity sensor 104 detects the acceleration status of the mobile device 10. As mentioned above, the biosensor 102 may keep detecting the relationship between the mobile device 10 and the user. Only when the mobile device 10 is carried by the user will the physical quantities provided by the gravity sensor 104 be utilized to determine whether the user is in an emergency. This is distinct from variations in the acceleration status when the mobile device 10 is not carried by the user (e.g. a mobile phone falls off a table, or the mobile phone is carried by the user in a backpack). After the control module 106 obtains information related to acceleration of the mobile device 10, the control module 106 may calculate the variation in the acceleration of the mobile device 10 during a specific period of time. When the user bumps into an object or falls over, a significant variation on the acceleration may be detected immediately; hence, the abovementioned specific period of time may be considered as an extremely short time. The control module 106 then sets a predetermined value for the variation (e.g. by writing the predetermined value into the program code 130), and determines whether the variation in acceleration of the mobile device 10 is greater than the predetermined value. When the variation is determined to be greater than the predetermined value, the control module 106 may determine that the user is in an emergency. If the variation is less than the predetermined value, the emergency is determined to not have occurred. In this case, the emergency detecting system may repeat steps 302-306 to keep monitoring whether the emergency occurs. The magnitude of the predetermined value may be determined arbitrarily. In a first embodiment, it may be determined according to a variation degree of the acceleration that may harm the user. The determination may also be performed by other methods, and is not limited herein. Finally, when an emergency occurs, the delivering devices D1-D3 may deliver corresponding alarm signals to notify the user or other people for follow-up assistance or handling, in order to achieve effective monitoring for personal safety.

Figure 4:
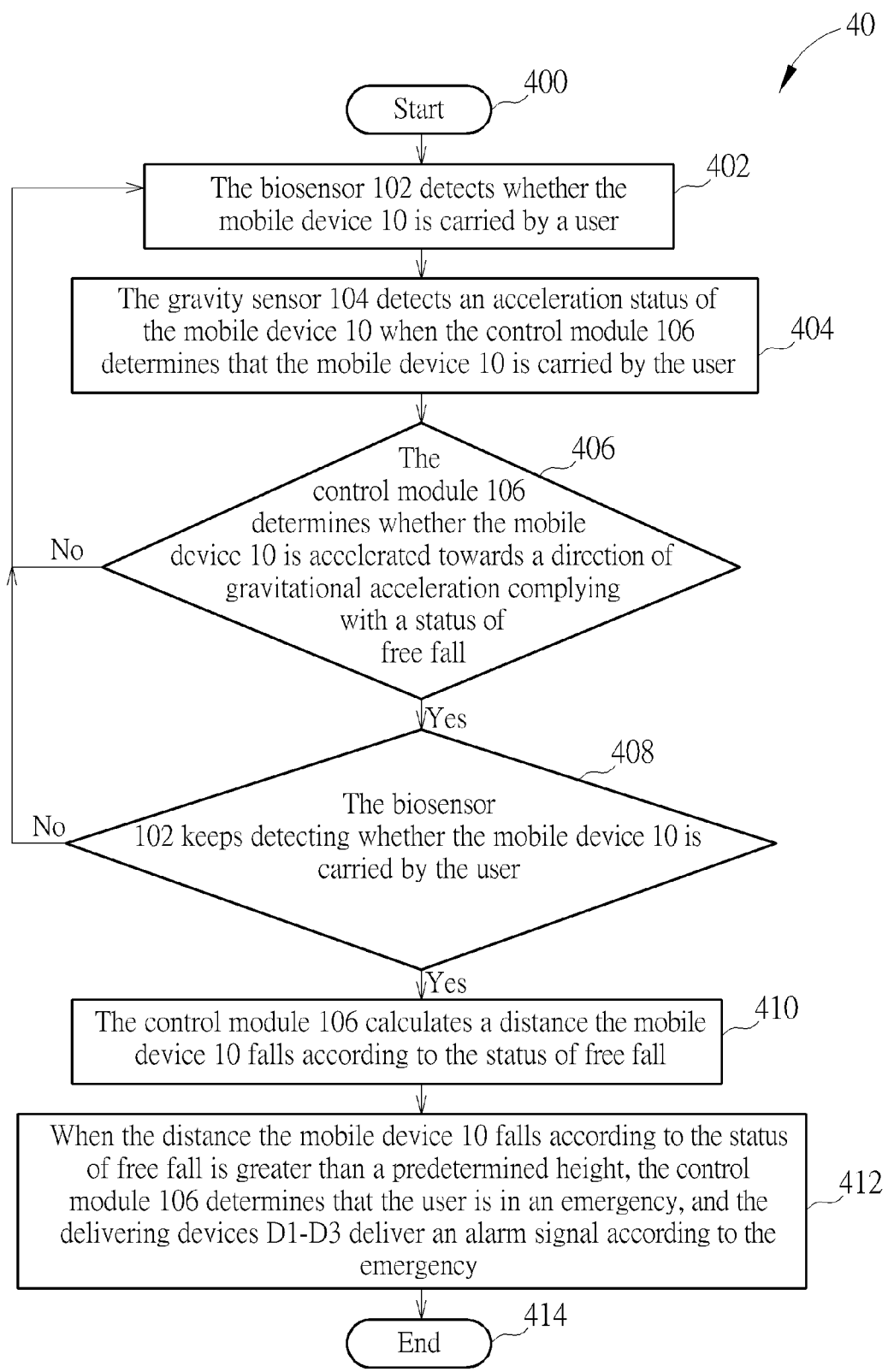
FIG. 4 is a schematic diagram of a further emergency detecting process according to an embodiment of the present disclosure.

Please refer to FIG. 4, which is a schematic diagram of a further emergency detecting process 40 according to an embodiment of the present disclosure. The emergency detecting process 40 may be utilized in the mobile device 10 and compiled into the program code 130 to be stored in the storage device 120. The emergency detecting process 40 may be realized in the above emergency detecting system, for the condition that the user falls from a height. The emergency detecting process 40 includes the following steps:

Step 400: Start.

Step 402: The biosensor 102 detects whether the mobile device 10 is carried by a user.

Step 404: The gravity sensor 104 detects an acceleration status of the mobile device 10 when the control module 106 determines that the mobile device 10 is carried by the user.

Step 406: The control module 106 determines whether the mobile device 10 is accelerated towards a direction of gravitational acceleration complying with a status of free fall. If yes, the flow proceeds to Step 408; otherwise, the process returns to Step 402.

Step 408: The biosensor 102 keeps detecting whether the mobile device 10 is carried by the user. If yes, the flow proceeds to Step 410; otherwise, the process returns to Step 402.

Step 410: The control module 106 calculates a distance the mobile device 10 falls according to the status of free fall.

Step 412: When the distance the mobile device 10 falls according to the status of free fall is greater than a predetermined height, the control module 106 determines that the user is in an emergency, and the delivering devices D1-D3 deliver an alarm signal according to the emergency.

Step 414: End.

According to the emergency detecting process 40, the biosensor 102 first detects whether the mobile device 10 is carried by the user. When the control module 106 determines that the mobile device 10 is carried by the user, the gravity sensor 104 detects the acceleration status of the mobile device 10. As mentioned above, the biosensor 102 may keep detecting the relationship between the mobile device 10 and the user. Only when the mobile device 10 is carried by the user will the physical quantities provided by the gravity sensor 104 be utilized to determine whether the user is in an emergency. This is distinct from variations in the acceleration status when the mobile device 10 is not carried by the user. After the control module 106 obtains information related to acceleration of the mobile device 10, the control module 106 may determine whether the mobile device 10 is accelerated towards the direction of gravitational acceleration complying with the status of free fall. When the mobile device 10 is determined to be accelerated towards the direction of gravitational acceleration complying with the status of free fall, the biosensor 102 will continue to detect whether the mobile device 10 is carried by the user. This step may be performed progressively for a period of time, in order to ensure that the user is indeed in an emergency and has fallen from a height rather than the mobile device 10 has been dropped. In general, if the user falls from a height and the mobile device 10 is carried by the user, the mobile device will fall together with the user for a period of time. Otherwise, in the condition that the mobile device 10 is dropped by the user, the biosensor 102 will detect immediately that the mobile device 10 is no longer carried by the user, which may not be considered as an emergency.

According to the above determination results, if the mobile device 10 progressively accelerates towards the direction of gravitational acceleration complying with the status of free fall and the mobile device 10 is progressively carried by the user, the control module 106 may calculate the distance the mobile device 10 falls according to the status of free fall. The control module 106 may set a predetermined height (e.g. by writing the predetermined height into the program code 130), and determines whether the distance the mobile device 10 falls is greater than the predetermined height. When the falling distance is determined to be greater than the predetermined height, the control module 106 may determine that the user is in an emergency. If the falling distance is less than the predetermined height, the emergency may be determined to not have occurred. In this case, the emergency detecting system may repeat steps 402-406 to keep monitoring whether the emergency occurs. The magnitude of the predetermined height may be determined arbitrarily. In a second embodiment, it may be determined to be a height great enough to cause injury to the user. The determination may also be performed by other methods, and is not limited herein. Finally, when an emergency occurs, the delivering devices D1-D3 may deliver corresponding alarm signals to notify the user or other people for follow-up assistance or handling, in order to achieve effective monitoring for personal safety.

The delivering devices D1-D3 may be of any type and may deliver the alarm signals using any methods. For example, the delivering devices D1-D3 may include a display screen of the mobile device 10, and the alarm signals may be shown on the screen. The delivering devices D1-D3 may also include a light disposed on the mobile device 10, which may be turned on to deliver the alarm signals when an emergency occurs. In a third embodiment, the alarm signals may be delivered by sound, and the delivering devices D1-D3 may include any acoustic devices of the mobile device 10. In other embodiments, the alarm signals may also be transmitted to the network terminal by using a networking device. Different types of the delivering devices D1-D3 and different delivering methods may coexist in one emergency detecting system. The user may select to use appropriate delivering devices and methods according to requirements, in order to achieve effective monitoring for personal safety.

Please note that the present disclosure is capable of providing a method of emergency detection which can determine whether the user is in an emergency according to the acceleration status of the mobile device when the mobile device is carried by the user, in order to enable immediate assistance or handling when the emergency occurs. As long as the mobile device is equipped with a biosensor (for detecting whether the mobile device is carried by the user) and a G-sensor (for detecting the acceleration status of the mobile device), the mobile device may be utilized for determining whether the user is in an emergency. Those skilled in the art can make modifications and alterations accordingly. For example, a mobile device may include any numbers of delivering devices, and the types of delivering devices may not be limited herein. The emergency detected by the present disclosure may include any conditions that may harm the user, which may include, but should not be limited to, falling over, bumping into something and falling from a height. A delivering device may deliver the alarm signal in the same form for all types of emergency, or may deliver different types of alarm signals corresponding to different types of emergencies. For example, for the two different emergencies of bumping into an object and falling from a height, the acoustic device may utilize a long alarm to correspond to the situation of bumping into an object and utilize a short alarm to correspond to the situation of falling from a height. In such a situation, after the user or others receive the alarm signal, they will know which kind of emergency has occurred and therefore be able to perform more effective and immediate assistance or handling.

The above emergency detecting method may be implemented in a non-transitory computer-readable storage medium. The non-transitory computer-readable storage media refer to any media that provide a plurality of instructions for execution of a processor. The media may be of many forms, which include, but should not be limited to, non-volatile and volatile media such as optical or magnetic disks, and dynamic storage devices, respectively. For example, common forms of computer-readable storage media may include a floppy disk, a hard disk drive, a magnetic type, any other magnetic medium, a CD-ROM, a digital video disk (DVD), any other optical medium, a RAM, a programmable ROM (PROM), an erasable programmable ROM (EPROM), a flash EPROM or any other memory chip.

In the prior art, most security monitoring products and applications are realized by using monitors or security systems. Coverage of such monitors and security systems, however, may not be satisfactory. If an accident or emergency occurs beyond the coverage of the monitors or security systems, the security monitoring systems may not be able to determine the circumstances and therefore cannot enable follow-up assistance or handling. In comparison, the present disclosure provides a method of utilizing a mobile device to detect an emergency. When the mobile device is carried by a user, the present disclosure can determine whether the user is involved in an emergency according to the acceleration status of the mobile device, so that assistance or processing can be performed immediately, in order to achieve effective monitoring for personal safety.

Those skilled in the art will readily observe that numerous modifications and alterations of the device and method may be made while retaining the teachings of the disclosure. Accordingly, the above disclosure should be construed as limited only by the metes and bounds of the appended claims.

What is claimed is:

1. A method of utilizing a mobile device to detect an emergency, comprising:
   detecting whether the mobile device is carried by a user via a biosensor together with a gravity sensor (G-sensor);
   detecting an acceleration status of the mobile device when the mobile device is determined to be carried by the user; and
   determining whether the user is in the emergency according to the acceleration status of the mobile device;
   wherein the step of determining whether the user is in the emergency according to the acceleration status of the mobile device comprises:
      determining whether the mobile device is accelerated towards a direction of gravitational acceleration complying with a status of free fall;
      when the mobile device is determined to be accelerated towards the direction of gravitational acceleration complying with the status of free fall, continuing to detect whether the mobile device is carried by the user;
      when the mobile device is determined to be progressively accelerated towards the direction of gravitational acceleration complying with the status of free fall and the mobile device is progressively carried by the user, calculating a distance the mobile device falls according to the status of free fall; and
      determining that the user is in the emergency when the distance the mobile device falls according to the status of free fall is greater than a predetermined height.

2. The method of claim 1, wherein the biosensor is a specific absorption rate (SAR) detector of the mobile device.

3. The method of claim 1, wherein the step of detecting the acceleration status of the mobile device is performed by the G-sensor of the mobile device.

4. The method of claim 1, wherein the step of determining whether the user is in the emergency according to the acceleration status of the mobile device comprises:
   calculating a variation in acceleration of the mobile device during a specific period of time, and determining whether the variation is greater than a predetermined value; and
   determining that the user is in the emergency when the variation is determined to be greater than the predetermined value.

5. The method of claim 4, wherein the emergency occurs when the user bumps into an object or falls over.

6. The method of claim 1, wherein the emergency occurs when the user falls from a height.

7. The method of claim 1, wherein the predetermined height is a height large enough to cause injury to the user.

8. The method of claim 1, further comprising delivering an alarm signal when the user is determined to be in the emergency.

9. The method of claim 8, wherein the step of delivering the alarm signal comprises displaying the alarm signal on a screen of the mobile device.

10. The method of claim 8, wherein the step of delivering the alarm signal comprises delivering the alarm signal via an acoustic device of the mobile device.

11. The method of claim 8, wherein the step of delivering the alarm signal comprises transmitting the alarm signal to a network via a networking device of the mobile device.

12. A non-transitory computer-readable storage medium, having a program executable by a processor to perform the method of detecting an emergency of claim 1.

13. An emergency detecting system used in a mobile device comprising:
   a biosensor, for detecting whether the mobile device is carried by a user;
   a gravity sensor (G-sensor), for detecting an acceleration status of the mobile device, and assisting the biosensor to detect whether the mobile device is carried by the user; and
   a control module, coupled to the biosensor and the gravity sensor, the control module comprising:
      a storage device, for storing a program; and
      a processor, for executing the program stored in the storage device, in order to perform the following steps:
         determining whether the mobile device is carried by the user; and
         determining whether the user is in an emergency according to the acceleration status of the mobile device when the mobile device is determined to be carried by the user;
   wherein the step of determining whether the user is in the emergency according to the acceleration status of the mobile device when the mobile device is determined to be carried by the user comprises:
      determining whether the mobile device is accelerated towards a direction of gravitational acceleration complying with a status of free fall;

when the mobile device is determined to be accelerated towards the direction of gravitational acceleration complying with the status of free fall, continuing to detect whether the mobile device is carried by the user;

when the mobile device is determined to be progressively accelerated towards the direction of gravitational acceleration complying with the status of free fall and the mobile device is progressively carried by the user, calculating a distance the mobile device falls according to the status of free fall; and determining that the user is in the emergency when the distance the mobile device falls according to the status of free fall is greater than a predetermined height.

14. The emergency detecting system of claim 13, wherein the biosensor is a specific absorption rate (SAR) detector of the mobile device.

15. The emergency detecting system of claim 13, wherein the emergency occurs when the user bumps into an object or falls over.

16. The emergency detecting system of claim 13, wherein the emergency occurs when the user falls from a height.

17. The emergency detecting system of claim 13, further comprising:

at least one delivering device, for delivering an alarm signal when the user is determined to be in the emergency.

* * * * *